United States Patent
Wu et al.

(10) Patent No.: US 10,779,739 B2
(45) Date of Patent: Sep. 22, 2020

(54) CONTACTLESS-TYPE SPORT TRAINING MONITOR METHOD

(71) Applicant: National Chiao Tung University, Hsinchu (TW)

(72) Inventors: Bing-Fei Wu, Hsinchu (TW); Chun-Hsien Lin, Hsinchu (TW); Po-Wei Huang, Hsinchu (TW); Tzu-Min Lin, Hsinchu (TW); Meng-Liang Chung, Hsinchu (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 82 days.

(21) Appl. No.: 16/040,721

(22) Filed: Jul. 20, 2018

(65) Prior Publication Data
US 2019/0246921 A1    Aug. 15, 2019

Related U.S. Application Data

(60) Provisional application No. 62/629,945, filed on Feb. 13, 2018.

(51) Int. Cl.
*A61B 5/024*    (2006.01)
*A61B 5/00*    (2006.01)
(Continued)

(52) U.S. Cl.
CPC ........ *A61B 5/02416* (2013.01); *A61B 5/0013* (2013.01); *A61B 5/0077* (2013.01); *A61B 5/024* (2013.01); *A61B 5/02125* (2013.01); *A61B 5/7203* (2013.01); *A61B 5/726* (2013.01); *A61B 5/7257* (2013.01); *A61B 5/7264* (2013.01); *A61B 5/7275* (2013.01);
(Continued)

(58) Field of Classification Search
CPC ... A61B 5/02416; A61B 5/024; A61B 5/7485; A61B 5/7275; A61B 5/7264; A61B 5/02125; A61B 5/0013; G06K 9/00302
USPC .......................................................... 382/118
See application file for complete search history.

(56) References Cited

U.S. PATENT DOCUMENTS

| 2014/0063236 A1* | 3/2014 | Shreve | G06K 9/00228 348/143 |
| 2016/0213303 A1* | 7/2016 | Hyde | A61B 5/1113 |

(Continued)

OTHER PUBLICATIONS

Bing-Fei Wu et al., "Camera-based Heart Rate Measurement Using Continuous Wavelet Transform", Jul. 21-23, 2017, IEEE.
(Continued)

*Primary Examiner* — Ayodeji O Ayotunde
(74) *Attorney, Agent, or Firm* — Bacon & Thomas, PLLC

(57) ABSTRACT

The present invention provides a contactless-type sport training monitor method, comprising: selecting at least an image database to recognize a plurality of expressions in the image database; making pre-processing for the plurality of expressions: using a convolutional neural network as a feature point extraction model; acquiring a human image; tracking a first target region and a second target region in the human image; making chrominance-based rPPG trace extraction; using the deep level model to compare the second target region image; and to calculate a post-exercise heart rate recovery achievement ratio, to judge the Rating of Perceived Exertion, and judging whether the human body is under overtraining status or not.

5 Claims, 3 Drawing Sheets

(51) Int. Cl.
  *G06K 9/00*   (2006.01)
  *G06F 3/01*   (2006.01)
  *A61B 5/021*  (2006.01)
  *G06T 7/246*  (2017.01)
  *A61B 5/0402* (2006.01)
  *G06T 7/20*   (2017.01)

(52) U.S. Cl.
  CPC .......... *A61B 5/7278* (2013.01); *A61B 5/7485* (2013.01); *G06F 3/017* (2013.01); *G06K 9/00302* (2013.01); *A61B 5/0402* (2013.01); *A61B 5/725* (2013.01); *A61B 5/7207* (2013.01); *A61B 2576/00* (2013.01); *G06T 7/20* (2013.01); *G06T 7/246* (2017.01)

(56) References Cited

U.S. PATENT DOCUMENTS

2016/0374567 A1* 12/2016 Breslow ............... A61B 5/4809
                     600/301
2019/0000391 A1* 1/2019 De Haan .............. A61B 5/7207

OTHER PUBLICATIONS

Po-Wei Huang et al., "Image Based Contactless Blood Pressure Assessment using Pulse Transit Time", Nov. 12-15, 2017, The 2017 International Automatic Control Conference (CACS 2017),IEEE.
Bing-Fei Wu et al., "A contactless sport training monitor based on facial expression and remote-PPG", Oct. 5-8, 2017, IEEE.

* cited by examiner

CONTACTLESS-TYPE SPORT TRAINING MONITOR METHOD

BACKGROUND OF THE INVENTION

1. Field of the Invention

The present invention relates to a contactless-type sport training monitor method, particularly to a contactless-type sport training monitor method by using an image method to monitor the heart rate and the facial expression, in order to judge integratedly whether the human body is under overtraining status or not.

2. Description of the Prior Art

A successful training program aims is to increase athletes' or exercisers' fitness and endurance. This is achieved by the application of the appropriate training protocols for athletes to reach high peak performance status during the competition season. However, overtraining may lead to fatigue, and limit athletes' performance. Sometimes the fatigue may even take the athletes several weeks to recover from. At this time, adjusting the training program becomes a very important topic.

Overtraining is characterized by imbalance between stress and recovery after exercising, and the syndrome is characterized by fatigue and low performance. At past, physicians, psychologists and physical therapists have tried to reach diagnosis and consensus regarding overtraining syndrome. The overtraining can be diagnosed by physiological, psychological and behavioral, neuro endocrinal and biochemical indicator, and immunological indicator etc.

The athletes' fitness and endurance should be considered during training program. Many clinical decision support systems can assist to monitor the factors of physiological signal, emotion, or the level of fatigue of the athletes' by some wearable devices. In addition, the questionnaire should also be taken into account to produce an assessment report. Such process is cumbersome, and the results are not objective. Furthermore, the person may feel uncomfortable when wearing the devices during the training program.

As the abovementioned description, the people expect to estimate the Rating of Perceived Exertion (RPE) without any wearable devices and questionnaires. A camera based heart rate detection algorithm and a fatigue expression feature extractor are fused to estimate the contactless-type Rating of Perceived Exertion (RPE) value. The results show that the heart rate detection algorithm and the fatigue heart rate detection can obtain the similar results of wearable devices. It means the contactless-type sport training monitor method has certain competitiveness.

Heart rate and fatigue facial expression are regarded as the index of overtraining. An image based overtraining monitoring system is proposed so that the training Rating of Perceived Exertion (RPE) level of the athlete can be estimated without any wearable devices. Since the questionnaire is not considered, the results would more objective.

To address the abovementioned problems, it is necessary to develop an appropriate method to achieve contactless-type monitoring heart rate and facial expression without any wearable devices attached on the athletes' body. This contactless-type method shall also be able to judge whether the athlete is under overtraining status or not by monitoring the fatigue, endurance and performance. The suitable measures shall be adopted to avoid the occurrence of overtraining status.

SUMMARY OF THE INVENTION

The embodiment of the present invention provides a contactless-type sport training monitor method, comprising: selecting at least an image database to recognize a plurality of expressions in the image database, respectively, in order to train a deep level model; making pre-processing for the plurality of expressions, using a convolutional neural network as a feature point extraction model in order to carry out the feature fusion for the plurality of expressions, in order to extract an expression feature, according to the expression feature to analyze the plurality of expressions as a facial expression image, and store in the deep level model; acquiring a human image; tracking a first target region and a second target region in the specific human facial image, and acquiring a first target region image in the first target region and a second target region image in the second target region, respectively; making chrominance-based rPPG (CHROM rPPG) trace extraction for the first target region image, making Fourier transform for the first target region image; making Peak Selection for the first target region image, to obtain a heart rate value (HR); using the deep level, model to compare the second target region image, to judge the second target region image as a specific facial expression image; and according to the specific expression to judge the heart rate value is a resting heart rate or an exercising heart rate and a lowest heart rate, to calculate a post-exercise heart rate recovery achievement ratio (ΔHRR), according to the post-exercise heart rate recovery achievement ratio to judge the Rating of Perceived Exertion (RPE), and judging whether the human body is under overtraining status or not.

In the preferred embodiment, the image database is YouTube, RaFD or ADFES.

In the preferred embodiment, training the deep level model includes using the blurring, sharpening, lightened and darkening treatment step to augment the plurality of expressions.

In the preferred embodiment, the dimension of the feature point extraction model is 128.

In the preferred embodiment, the facial expression image is selected from the group consisting of anger, disgust, fear, happiness, sadness or surprise.

In the preferred embodiment, first target region image is the palm skin image or face skin image of the human image.

In the preferred embodiment, the second target region image is the specific facial expression image.

In the preferred embodiment, the Peak Selection steps comprise a motion noise spectrum stability value is lower than a stability threshold, or the difference between largest frequency and motion frequency is smaller than a frequency threshold.

In the preferred embodiment, the stability threshold is −11 bpm, and the frequency threshold is 4.5 bpm.

In the preferred embodiment, the motion noise spectrum stability value is $$10\log\left[\frac{E_1}{E_2}\right],$$

wherein, $E_1$ is the largest frequency energy, and $E_2$ is the total signal energy minus $E_1$.

In the preferred embodiment, the post-exercise heart rate recovery achievement ratio is $$\frac{E[HR_{ex}] - HRR_{lowest}}{E[HR_{ex}] - E[HR_{rest}]},$$

wherein, $HRR_{lowest}$ is the lowest heart rate value, $E[HR_{ex}]$ is the average exercising heart rate value, and $HR_{rest}$ is the average resting heart rate value.

In order to further understand the features and technological content of the present invention, please refer to the following detailed description and attached figures of the present invention. Nevertheless, the attached figures are used for reference and description, which are not used for limiting the present invention.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

In the following context, the specific embodiments are used to describe the contactless-type sport training monitor method of the present invention. The people who are familiar to this art can understand the advantages and efficacies of the present invention easily from the content disclosed in this article. The present invention can also be implemented or applied by other different embodiments. Every detail in this article can also be modified and changed based on different viewpoints and applications without violating the spirit of the present invention. In addition, the figures in the present invention are only brief description, and they are not drawn in actual dimension to reflect the actual size. The following description of preferred embodiment describes the viewpoint of the present invention in more detail, which will not limit the scope of the present invention by any viewpoint.

Figure 1:
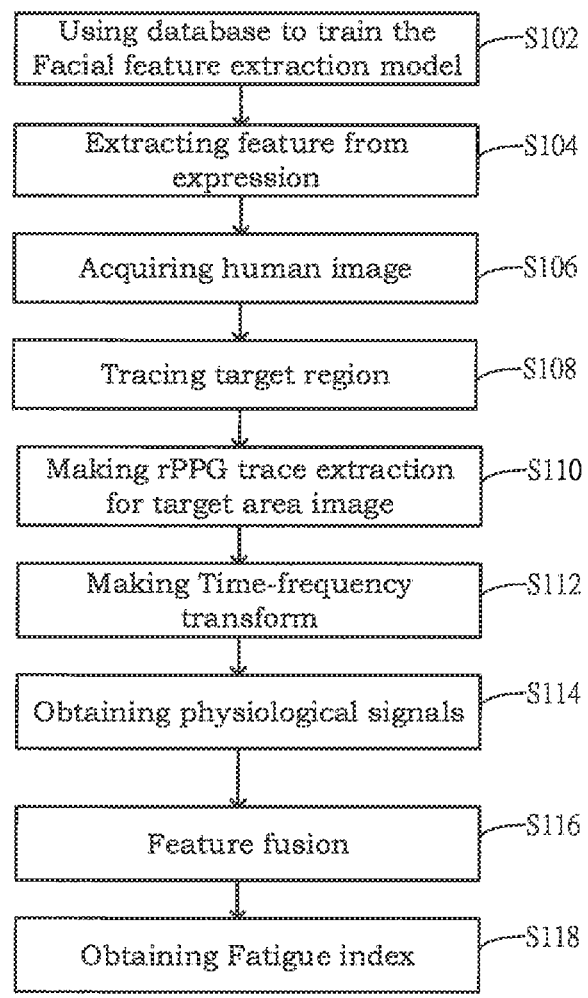
FIG. 1 illustrates a flowchart of contactless-type sport training monitor method of the present invention.
Figure 2:
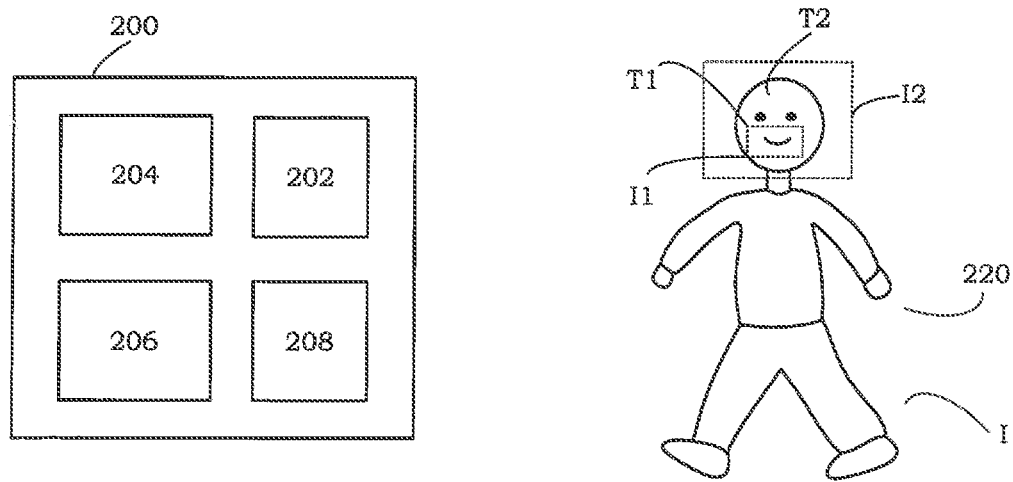
FIG. 2 illustrates a contactless-type sport training monitor device of the present invention.

Please refer to FIG. 1 and FIG. 2. FIG. 1 illustrates a flowchart of contactless-type sport training monitor method of the present invention. FIG. 2 illustrates a contactless-type sport training monitor device of the present invention. The contactless-type sport training monitor method of the present invention shown in FIG. 1 comprises the following steps:

Firstly, as shown in Step S102 of FIG. 1, selecting an image database 204 to recognize a plurality of expressions in the image database 204, respectively, in order to train a facial expression feature extraction model. It has to describe that the image database is YouTube, RaFD or ADFES. The image database is used to train a facial expression feature extraction model. The videos are downloaded from the image database, which are cropped with the time interval set to 1, 2 or 3 seconds to produce the facial images. The face images would be filtered out if it is non-face, two-face, or too blurred, or too dark, or the expressions which are hard to be identified. In addition, because the environment condition of YouTube image database is quite bad, the RaFD or ADFES image database is added to train the image database of deep level model in the embodiment. The training images of deep level model would be augmented by blurring, sharpening, lightened and darkening.

Please also refer to FIG. 3. FIG. 3 illustrates the Neighbor-center difference image method of the present invention. As shown in FIG. 3, it is able to increase the edge efficiency of the plurality of first expression P1.

As shown in Step S104 of FIG. 1 and also refer to FIG. 2, a convolutional neural network feature paint is used to extract model 208 to obtain an expression feature from expression P. According to the expression feature, analyze the plurality of expressions as a facial expression image, and store in the facial expression feature extraction model 206 in FIG. 2. As an example in FIG. 3, when the feature point extraction model 208 analyze and judge the expression feature extracted from expression P as a happy facial expression image, the happy facial expression image is stored in the facial expression feature extraction model 206. It has to note that the dimension of feature point extraction model is 128. The facial expression image is selected from the group consisting of anger, disgust, fear, happiness, sadness or surprise.

Still as shown in Step S106 of FIG. 1, the image device 202 of FIG. 2 is used to extract the human image I of human body 220.

As shown in Step S108 of FIG. 1, tracking the first target region T1 and the second target region T2 in the human image I, and acquiring the first target region image I1 of the first target region T1, and the second target region image I2 of the second target region T2 respectively, as shown in FIG. 2. It has to note that the first target region image I1 is the palm skin image or facial skin image of human image I. The second target region image I2 is the specific facial expression image, as shown in FIG. 2.

As shown in Step S110 of FIG. 1, making the chrominance-based rPPG (CHROM rPPG) trace extraction for the first target region image I1. The CHROM rPPG trace extraction is passing an assumed standard skin color to enhance the robustness of motions and eliminate the noise generated in the motion (such as swing) domain.

As shown in Step S112 of FIG. 1, making Fast Fourier Transform (FFT) for the first target region image I1 to transform to the domain.

As shown in Step S114 of FIG. 1, making Peak Selection for the first target region image I1, to obtain a heart rate value HR. The Peak Selection is used to reduce the motion noise, so a Spectrum Stability (SS) is defined as:

$$SS = 10\log\left[\frac{E_1}{E_2}\right],$$

Wherein, $E_1$ is the energy of the largest frequency, and $E_2$ is the total signal energy minus $E_1$.

As shown in the embodiment of FIG. 1, the Peak Selection Step includes the spectrum stability value of motion noise is lower than a stability threshold $T_h$, or the difference between largest frequency $f_h$ and motion frequency $f_{ex}$ smaller than a frequency threshold $T_f$.

As shown in the embodiment of FIG. 1, the bandwidth of stability threshold $T_h$ is −11 bpm, and the bandwidth of frequency threshold $T_f$ is 4.5 bpm.

Figure 3A:
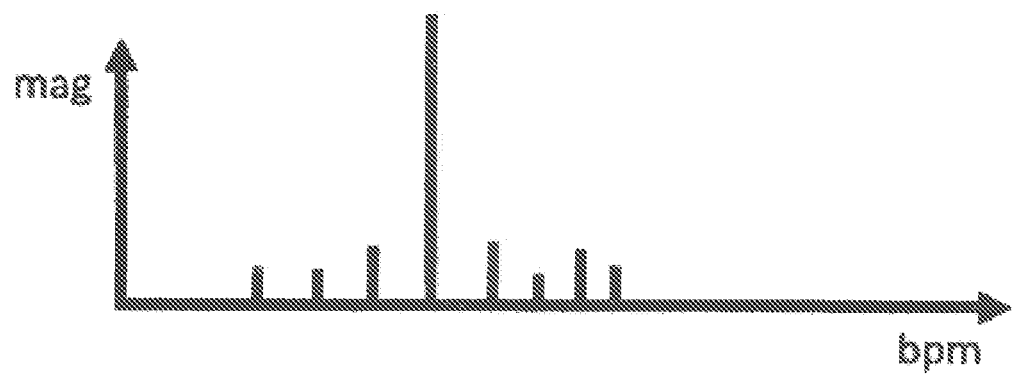
FIG. 3A illustrates the heart rate spectrum with high spectrum stability of the present invention.
Figure 3B:
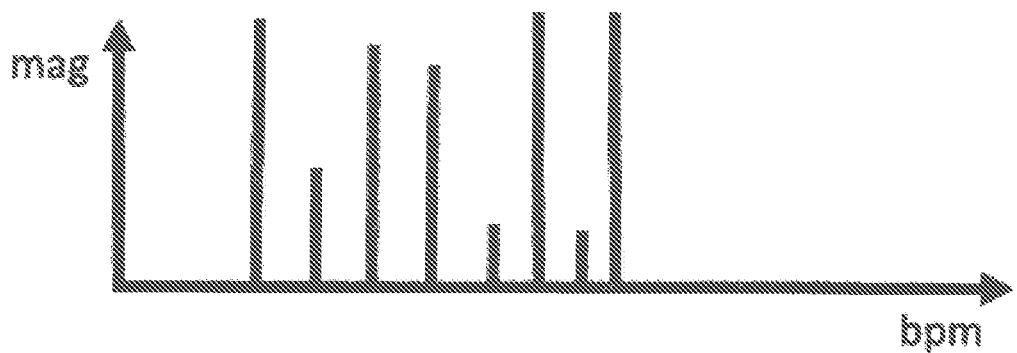
FIG. 3B illustrates the heart rate spectrum with low spectrum stability of the present invention.

Please refer to FIG. 3A and FIG. 3B. FIG. 3A illustrates the heart rate spectrum with high spectrum stability of the present invention. FIG. 3B illustrates the heart rate spectrum with low spectrum stability of the present invention.

As shown in Step S116 of FIG. 1, the deep level model is used to compare the second target region image I2, to judge the second target region image I2 is a specific expression.

As shown in Step S118 of FIG. 1, according to the specific expression to judge whether the heart rate value HR is resting heart rate $HR_{rest}$, or exercising heart rate $HR_{ex}$, and lowest heart rate $HRR_{lowest}$, to calculate the post-exercise heart rate recovery achievement ratio ΔHRR. According to the post-exercise heart rate recovery achievement ratio ΔHRR to judge the Rating of Perceived Exertion (RPE), and judge whether the human body is under the overtraining status or not. The post-exercise heart rate recovery achievement ratio ΔHRR is defined as:

$$\Delta HRR = \frac{E[HR_{ex}] - HRR_{lowest}}{E[HR_{ex}] - E[HR_{rest}]}$$

Wherein, $HRR_{lowest}$ is the lowest heart rate value, $E[HR_{ex}]$ is the average exercising heart rate value, $HR_{rest}$ is the average resting heart rate value.

By the invention, the people can estimate the Rating of Perceived Exertion (RPE), i.e., a camera based fatigue heart rate detection algorithm and a fatigue facial expression image feature extractor are fused to estimate the contactless-type Rating of Perceived Exertion (RPE) value. Therefore, the invention operating the fatigue heart rate detection, and a fatigue facial expression image feature extractor can obtain the similar results of wearable devices and the questionnaires.

Indeed, the invention can achieve the contactless-type monitoring heart rate and the facial expression image without any wearable devices attached on the athletes' body. Therefore, the invention, which is the contactless-type method exactly can judge whether the athlete is under overtraining status or not.

It is understood that various other modifications will be apparent to and can be readily made by those skilled in the art without departing from the scope and spirit of the invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which the invention pertains.

What is claimed is:

1. A contactless-type sport training monitor method by using a human image and a physiological signal, comprising:

selecting at least an image database to recognize a plurality of expressions in an image database, respectively, in order to train a facial expression feature extraction model;

acquiring a sequence of human images;

tracking a first target region and a second target region in said human image, and acquiring a first target region image in said first target region and a second target region image in said second target region, respectively, wherein the first target region image comprises a palm skin image or a face skin image of said human image, and said second target region image comprises a facial expression image;

making a rPPG trace extraction for said first target region image:

making a time-frequency transform for said first target region images;

using a signal processing for said first target region image, to obtain some physiological signals, wherein said signal processing uses a motion noise spectrum stability value that is lower than a stability threshold, or a difference between a largest frequency and a motion frequency that is smaller than a frequency threshold, wherein said motion noise spectrum stability value comprises $$10\log\left[\frac{E_1}{E_2}\right],$$

and wherein E1 is a largest frequency energy, and E2 is a total signal energy minus E1, and wherein said physiological signals comprise a heart rate, a heart rate recovery, and a post-exercise heart rate recovery achievement ratio comprising $$\frac{E[HR_{ex}] - HRR_{lowest}}{E[HR_{ex}] - E[HR_{rest}]},$$

wherein $HRR_{lowest}$ comprises a lowest heart rate value, $E[HR_{ex}]$ comprises an average exercising heart rate value, and $HR_{rest}$ comprises an average resting heart rate value;

using said facial expression feature extraction model to extract the facial expression features on the said second target region images; and using said facial features and said physiological signals to obtain an index for judging whether said human body is under overtraining status or not.

2. The contactless-type sport training monitor method according to claim 1, wherein the image database can be YouTube, RaFD and ADFES.

3. The contactless-type sport training monitor method according to claim 1, wherein the facial expression feature extraction model can be a convolutional neural network.

4. The contactless-type sport training monitor method according to claim 1, wherein the facial expression feature extraction model can be trained by specific facial expressions consisting of anger, disgust, fear, happiness, sadness, surprise, and contempt, or by an action unit coding system or an index of valence and arousal.

5. The contactless-type sport training monitor method according to claim 1, wherein the stability threshold comprises −11 bpm, and the frequency threshold is 4.5 bpm.

* * * * *